United States Patent [19]
Dehan et al.

[11] Patent Number: 5,853,710
[45] Date of Patent: Dec. 29, 1998

[54] SHAVE GEL COMPOSITION

[75] Inventors: Louis Dehan, Seraing; Didier Juprelle, Sluizen, both of Belgium

[73] Assignee: Colgate-Palmolive Co., New York, N.Y.

[21] Appl. No.: 938,303

[22] Filed: Sep. 26, 1997

[51] Int. Cl.$^6$ ..................................... A61K 7/15
[52] U.S. Cl. ........................ 424/73; 424/401; 514/944; 514/785; 514/784; 514/781
[58] Field of Search .............................. 424/73, 401, 70.1

[56] References Cited

FOREIGN PATENT DOCUMENTS 9422415  10/1994  WIPO .

*Primary Examiner*—Thurman K. Page
*Assistant Examiner*—James M. Spear
*Attorney, Agent, or Firm*—Martin B. Barancik

[57] ABSTRACT

A nonaerosol shave gel composition comprising a) about 12 to 30 wt. % of amine salts of a mixture of lauric acid, myristic acid, and palmitic acid wherein the weight ratio of the myristic acid to the lauric acid and palmitic acid is respectively about 2.5 to about 3.75:1:1, b) about 1 to 3 wt. % of a sugar ester of a long-chain alkyl carboxylic acid having from about 8 to about 18 carbon atoms, inclusive, c) about 2 to about 4 wt. % of an ethoxylated emollient, slip agent, d) about 1 to about 2 wt. % of an ethoxylated alkyl glycoside ester of a diacid having an alkyl group of about 8 to about 18 carbon atoms, and e) about 0.3 to 0.9 wt. % of a cellulosic gellation agent.

20 Claims, No Drawings

SHAVE GEL COMPOSITION

BACKGROUND OF THE INVENTION

Various methods of removing hair from the body have been employed for generations. Most of these methods involve a sharp tool for actual hair removal. Assisting in the removal is a chemical composition which makes hair removal easier. These compositions usually include a surfactant material, emollients to make the skin feel better, slip agents for the tool to slide over the skin in an easier manner, lubricity enhancing agents to bring about a better skin feel during and after the hair removal process as well as a carrier.

Such shave assisting compositions are present in many delivery forms. They can be present as a post foaming gel, that is the gel is expressed from the container and then foams as it is rubbed into the portion of the skin from which the hair is to be removed. Other forms are merely simple shave creams or the traditional soap bar which can be lathered in a mug-shaped vehicle. With respect to the gels, they are usually expressed from the container by an aerosol delivery system. However, this is a relatively expensive form of delivery in that it requires a dual pack container which can withstand a considerable amount of pressure and also utilizes propellants which may be potentially damaging to the skin or to the environment.

Therefore, there exists a need for a non-aerosol shave gel which has the above-mentioned abilities of skin cleansing, skin conditioning, slip, and lubricity while being essentially non-irritating. Additionally, the non-aerosol nature of such a composition allows it to be packaged in a non-pressurized container. Additionally, it has a further benefit of being able to be packaged in a deformable container which allows for the delivery to the skin of a predetermined, specific amount of material. Such containers can be simple squeeze tubes or any other container which can deliver the shave gel by appropriate pressure on the surface of the container or through a valve which allows the composition to be delivered through the pressure created by the hand creating a pumping action.

SUMMARY OF THE INVENTION

In accordance with the invention there is a shave gel composition comprising about 12 to about 30% of amine salts of a mixture of lauric acid, myristic acid, and palmitic acid wherein the weight ratio of the myristic acid to the lauric acid and palmitic acid is a) about 2.5 to about 3.75:1:1, respectively, b) about 1 to 3 wt. % of a sugar ester of a long-chain alkyl carboxylic acid having from about 8 to about 18 carbon atoms, c) about 2 to about 4 wt % of an ethoxylated emollient and slip agent, d) about 1 to about 2 wt. % of an ethoxylated alkyl glycoside ester of diacid having alkyl group from about 8 to about 18 carbon atoms and e) about 0.3 to 0.9% of a cellulosic gellation agent.

The gel is preferably clear as measured by clarity to the eye. It has also been determined that generally no more than about 1% of the gellation agent should be employed since above this point a sticky skin feel occurs. Additionally, the levels of the specific emollients have been selected so that foam generation is not significantly affected.

DETAILED DESCRIPTION OF THE INVENTION

The amine salt form of the long-chain alkyl carboxylic acids is utilized. Examples of such amines include ammonium, triethylamine, triethanolamine and the like. The preferred amine salt is triethanol amine. It is preferred in the composition to maintain a slight excess of triethanolamine necessary to neutralize the long-chain alkyl carboxylic acids. This additional free triethanolamine helps to bring about product clarity. The acid ratio of the amine salts is preferably about three parts of myristic acid to one part each of the palmitic and lauric acid. Other long-chain alkyl carboxylic acids in their amine salt forms can also be present. For example, the amine salt of stearic acid can also be present in the composition. When stearic acid as the salt is present, the ratio of the acids remain the same, that is the myristic should be present also in about a 2.5 to 3.75, preferred 3.0, ratio as weight parts to one part of the stearic acid as well as the palmitic and lauric in the composition. Preferred quantities of the amine salts in the composition are from about 15 to about 25 wt. %.

The sugar esters of the long-chain carboxylic acid function primarily as a nonionic surfactant and provide appropriate skin conditioning and feel. The sugar portion of the ester can be derived from sucrose, fructose, xylose, and the like. The long-chain fatty acid has alkyl from approximately 8 to about 18 carbon atoms including the carbon of the carboxylic acid. Sucrose is the preferred sugar. Cocoacid is the preferred acid thereby forming the most preferred ester, sucrose cocoate.

Also present in the composition is an ethoxylated emollient which provides slip and lubricity. Various emollients can be used, for example Laureth-23, and Oleth-20. The preferred emollient, in this case, is lanolin with about 40 to about 100 ethoxy groupings. Particularly preferred is PEG 75 lanolin.

The composition is in gellular form and therefore requires gellation agents to be present. The alkylated sugar ester of a long-chain acid preferably together with cellulosic material brings about gellation of the composition. With respect to the alkyl sugar ester of a long-chain acid, the alkyl group is preferably methyl, the sugar is glucose and the acid is dioleic. It is most preferable that the composition also be ethoxylated so as to present the appropriate dispersion and skin feel within the composition. Generally from about 50 to about 200 ethoxy groups are present, preferably 75 to about 150. The most preferable compound is PEG-120 methyl glycoside dioleate. The cellulose derivative which can be employed is a hydroxy alkylated material, up to 4 carbon atoms in length, preferably hydroxy ethyl cellulose. Preferably together, these two agents provide the appropriate gellation characteristics to the composition and also provide the type of lubricity and slip, which is particularly favored in shave gels. In these particular compositions it is important to maintain a balance between the gellation properties and the skin feel or slip. When using hydroxy ethyl cellulose as a gellation agent, it is important to maintain the concentration in the composition for the hydroxyethyl cellulose below or equal to about one wt. %. Above this quantity the skin feel is adverse and seems to be sticky. This can also clearly present problems when shaving. A preferable range is about 0.4 to about 0.8 wt. %. Additionally, the ethoxylated alkyl sugar ester of the long-chain acid should be maintained below about 2 wt. % composition. If above about 2 wt. % of the composition, the generation of foam upon agitation of the gel can be adversely affected.

Other additional materials can be present in the composition, Additional surfactants can be present in order to provide further lather and boost the foam. Particularly preferred are the laureth sulfates particular with 2 or 3 ethoxy groups and the mild foam boosting betaines such as the long-chain alkylamido ethyl or propyl betaines, particularly cocoamido propyl betaine. Depending on the proper balance that one wishes to see among the characteristics of the gel one can use these additional surfactants in relatively small amounts, for example, 1 to 3 wt. % of the composition of the laureth sulfate and about 1 to about 2 wt. % of the betaine. Additionally, humectants can be utilized. These provide appropriate skin feel plus lubricity and give density and creaminess to the foam. Among these humectants which can be utilized are glycerine, ethylene glycol, sorbitol and propylene glycol. Glycerin is the preferred material. About 3 to about 7 wt. % can be employed in the composition, preferably about 4 to about 6.5 wt. %.

A particularly preferred additional material is a polyethylene glycol of relatively high molecular weight, generally about 400,000 to about 1,000,000, preferably about 500,000 to about 700,000. Most preferred is a polyethylene glycol of a molecular weight of about 600,000 commercially available as PEG-14M.

The pH of the composition is generally on the basic side of neutral, preferably from about 8.0 to about 8.8, more preferably not above about 8.5. The viscosity is generally from about 20,000 to about 50,000 cps, preferably from about 25,000 to about 35,000 cps. Viscosity is measured on a Brookfield RVT using spindle no. 5 at 10 rpm.

The balance of the composition is generally water. Other materials may also be present such as preservatives, antibacterial agents, antioxidants, and colorants if desired. The composition is prepared by mixing the components together and filling a deformable container such as a tube. The gel can be applied to the skin by either brush, sponge, or other applicator, or the fingers, thereby working up a lather.

Below are examples of the invention. These examples are intended to illustrate the broad concept of the invention and not unduly limit it.

EXAMPLE 1

The following examples are prepared with the triethanolamine reacting with the long-chain acids to prepare the triethanolamine salts thereof. The excess triethanolamine helps maintain the clarity of the gel.

| Component | Wt. % |
|---|---|
| Myristic acid | 6.9 |
| Lauric acid | 2.3 |
| Palmitic acid | 2.3 |
| Sucrose cocoate | 2.0 |
| PEG 75 Lanolin | 3.0 |
| PEG - 14 M | 0.15 |
| PEG - 120 methyl glycoside dioleate | 1.5 |
| Dodecanol | 0.2 |
| Sodium Laureth Sulphate 2EO (70%) | 3.0 |
| Cocamidopropyl betain | 1.88 |
| Hydroxyethylcellulose | 0.5 |
| Sorbitol (70%) | 3.0 |
| Triethanolamine | 7.83 |
| Aloe vera | 0.2 |
| Fragrance | 0.9 |
| Dye | 0.0005 |
| Water | Balance |

This composition has excellent skin feel attributes but is somewhat weak on lather attributes when tested against a marketed concentrated gel in a consumer test.

EXAMPLE 2

| Component | Wt. % |
|---|---|
| Stearic acid | 2.25 |
| Palmitic acid | 2.25 |
| Myristic acid | 8.0 |
| Lauric acid | 3.0 |
| Sucrose cocoate | 2.0 |
| PEG 75 Lanolin | 3.0 |
| PEG - 14 M | 0.15 |
| PEG - 120 methyl glycoside dioleate | 1.87 |
| Hydroxyethylcellulose | 0.5 |
| Glycerine | 6.0 |
| Triethanolamine | 10.2 |
| Fragrance | 0.6 |
| Dye | 0.0005 |
| Water | Balance |

Greater lather is obtained with Example 2 than Example 1. Utilizing a collagen swelling test, the potential of skin irritation is evaluated.

This test concept and test system is generally described in:
J. C. Blake-Haskins, D. Scala, L. D. Rhein and C. R. Robbins PREDICTING SURFACTANT IRRITATION FROM THE SWELLING RESPONSE OF A COLLAGEN FILM. J. Soc. Cosmet. Chem. 37, 199–210 (July.August 1986)

Our test protocol is described in:
Morrison, M. and Paye, M. A COMPARISON OF THREE IN VITRO SCREENING TESTS WITH AN IN VIVO CLINICAL TEST TO EVALUATE THE IRRITATION POTENTIAL OF ANTIBACTERIAL LIQUID SOAPS. J. Soc. Cosmet. Chem. 46, 291–299 (November, December 1995) and is generally performed as follows: a piece of collagen sheet (1 cm2) from Colla-Tech (Plainsboro, N.J.) is incubated for 24 hours, at 50° C., with a solution of the finished product at 1% of the dry extract at its own pH. The collagen is weighed before and after incubation to determine the amount of swelling. The more the collagen swells, the more irritating the product. The results are expressed in % of swelling.

| Composition | % Swelling |
|---|---|
| Palmolive Shave Cream | 1010 |
| Gillette Concentrated Shave Gel | 1190 |
| Example 1 | 460 |
| Example 2 | 153 |

Both of the Example compositions test milder than the marketed shave cream and the concentrated gel. Example 2 is milder than Example 1 in this test system.

What is claimed is:

1. A nonaerosol shave gel composition comprising
   a) about 12 to 30 wt. % of amine salts of a mixture of lauric acid, myristic acid, and palmitic acid wherein the weight ratio of the myristic acid to the lauric acid and palmitic acid is respectively about 2.5 to about 3.75:1:1,
   b) about 1 to 3 wt. % of a sugar ester of a long-chain alkyl carboxylic acid having from about 8 to about 18 carbon atoms, inclusive,
   c) about 2 to about 4 wt. % of an ethoxylated emollient, slip agent,
   d) about 1 to about 2 wt. % of an ethoxylated alkyl glycoside ester of a diacid having an alkyl group of about 8 to about 18 carbon atoms, and
   e) about 0.3 to 0.9 wt. % of a cellulose gelling agent.

2. The composition in accordance with claim 1 wherein the gel is clear.

3. The composition in accordance with claim 2 wherein the composition is packaged in a deformable tube.

4. The composition in accordance with claim 2 wherein about 15 to about 25 wt. % of a) is present.

5. The composition in accordance with claim 2 wherein free amine is present.

6. The composition in accordance with claim 5 wherein the amine is triethanolamine.

7. The composition in accordance with claim 2 wherein stearic acid is also present, the myristic acid to stearic acid weight ratio is about 2.5 to 3.75:1.

8. The composition in accordance with claim 1 wherein in b) the sugar is sucrose, xylose or fructose and the long-chain acid has from about 12 to about 18 carbon atoms.

9. The composition in accordance with claim 8 wherein b) is sucrose cocoate.

10. The composition in accordance with claim 1 wherein c) is an ethoxylated lanolin with about 40 to about 100 ethoxy groups.

11. The composition in accordance with claim 10 wherein c) is PEG 75 lanolin.

12. The composition in accordance with claim 1 wherein in d) the alkyl is methyl and the ethoxy group is an average of from about 75 to about 150.

13. The composition in accordance with claim 12 wherein d) is PEG-120 methyl glycoside dioleate.

14. The composition in accordance with claim 1 wherein e) is a hydroxy alkyl cellulose with alkyl of 1 to 4 carbon atoms, inclusive.

15. The composition in accordance with claim 14 wherein e) is hydroxyethyl cellulose.

16. The composition in accordance with claim 15 wherein the maximum amount of hydroxyethyl cellulose is about 0.7 wt. %.

17. The composition in accordance with claim 1 wherein a humectant is also present.

18. The composition in accordance with claim 17 wherein the humectant is glycerine.

19. The composition in accordance with claim 17 wherein glycerine is present in from about 3 to about 7 wt % of the composition.

20. The composition in accordance with claim 17 wherein glycerine is present in the composition in from about 3 to about 6 wt % of the composition.

* * * * *